United States Patent [19]

Ansorge

[11] Patent Number: 4,836,244

[45] Date of Patent: Jun. 6, 1989

[54] DEVICE FOR THE INJECTION OF VERY SMALL AMOUNTS OF SAMPLES INTO CELLS

[75] Inventor: Wilhelm Ansorge, Gaiberg, Fed. Rep. of Germany

[73] Assignee: Europaisches Laboratorium fur Molekularbiologie, Fed. Rep. of Germany

[21] Appl. No.: 742,713

[22] Filed: Jun. 7, 1985

Related U.S. Application Data

[62] Division of Ser. No. 460,101, Jan. 21, 1983, Pat. No. 4,532,205.

[30] Foreign Application Priority Data

Feb. 5, 1982 [DE] Fed. Rep. of Germany ....... 3204040

[51] Int. Cl.⁴ ............................................. F17D 3/05
[52] U.S. Cl. .................................... 137/557; 137/597; 137/599; 251/295; 604/118
[58] Field of Search ............... 137/557, 597, 599, 883, 137/505.12; 422/81; 604/118, 147; 251/295

[56] References Cited

U.S. PATENT DOCUMENTS

| 2,679,207 | 5/1954 | Mategorin | 137/599 X |
| 3,471,674 | 10/1969 | Gage | 137/559 X |
| 3,477,467 | 11/1969 | Sewell et al. | 137/599 |
| 3,633,239 | 1/1972 | Meyerhoefer | 137/599 X |
| 4,004,718 | 1/1977 | Wesley | 222/386 |
| 4,111,677 | 9/1958 | Andrews | 65/271 |
| 4,456,223 | 6/1984 | Ebling | 137/599 X |

FOREIGN PATENT DOCUMENTS 32719 7/1981 European Pat. Off. .
1909703 9/1969 Fed. Rep. of Germany .
2145962 3/1973 Fed. Rep. of Germany .
2604166 8/1977 Fed. Rep. of Germany .
2152490 4/1973 France .
1526761 9/1978 United Kingdom .

OTHER PUBLICATIONS

Graessmann et al, Methods in Enzymology, vol. 65, (1980), pp. 816-825.
Stacey, "Microinjection of mRNA and other Macromolecules into Living Cells" in Buch, *Methods in Enzymology*, vol. 79B, pp. 76-88, (1981).
Chem. Abstracts 92:193643t, (1980).
Chem. Abstracts 94:1675b, (1981).
Mueller et al-Trends Biochem. Sci. (Pers. Ed.), (1980, vol. 5, No. 3, pp. 60-62.

Primary Examiner—Stephen Hepperle
Attorney, Agent, or Firm—Wood, Dalton, Phillips, Mason & Rowe

[57] ABSTRACT

A method and a device are proposed for the injection of very small amounts of samples into cells (74) with the aid of a microcapillary (10). During the injection, a constant injection pressure of about 0.12 bar, provided by a pressurized cylinder (46) is applied ot the microcapillary (10), which is reduced after the completion of the injection to a holding pressure of 0.02 bar until the next cell (64) is to be injected. A high-pressure ($p_1$) supplied from another pressurized cylinder (44) serves for blowing out the microcapillary tip (12). A three-way valve (42) permits simple and rapid switching between the various pressure ($p_1$, $p_2$ and $p_3$). Reproducible amounts of sample in the range from $10^{-11}$ ml to $10^{-13}$ ml can be injected reprodicibly, simply and rapidly.

5 Claims, 4 Drawing Sheets

DEVICE FOR THE INJECTION OF VERY SMALL AMOUNTS OF SAMPLES INTO CELLS

This is a division of application Ser. No. 460,101 filed on Jan. 21, 1983 now U.S. Pat. No. 4,532,205.

The invention is concerned with a process for the injection of very small amounts of samples especially into cells, with the aid of microcapillary, one of the capillary ends of which has a tip with an inside diameter in the μm region; the microcapillary is filled with the sample fluid and during the injection an injection pressure is applied to the inside space of the capillary from the other end of the capillary to make the test liquid flow out from the tip.

In a known method of this type (Graessmann, A., Graessmann, M. and Müller, C., "Methods in enzymology", Volume 65 (1980), pages 816 to 825), the inside space of the capillary is attached to a hand syringe. In order to inject the sample amount, pressure is applied to the syringe piston by hand for an appropriate length of time. However, it was found that frequently after a number of cells have been inoculated, the tip of the microcapillary becomes plugged and a new microcapillary must be used.

In contrast, it is the purpose of the invention to reduce the danger of plugging of the microcapillary tip during use as much as possible in a method such as that mentioned above.

This task is solved by reducing the pressure inside the capillary after the injection of the desired amount of sample to a holding pressure which is different from zero and is lower than the injection pressure at which substantially no sample fluid flows from the tip and then this holding pressure is maintained until the beginning of the next injection. It was found that this holding pressure reliably prevents blocking of the tip during repeated injections.

A holding pressure, which is 0.1 to 0.5 times, preferably 0.2 to 0.3 times and most preferably about 0.25 times the injection pressure was found to be especially effective.

In order to accelerate the first flow of the sample fluid contained in the inside space of the capillary and possibly to prevent initial blocking of the tip, it is proposed that, after filling the sample fluid into the capillary and before the first injection, a higher pressure be applied to the inside space of the capillary, a pressure which is greater than the injection pressure. In order to prevent blocking or formation of deposits inside the capillary tip even when a large number of injections are made in succession, it is proposed that the high pressure be applied to the inside space of the capillaries repeatedly, after several injections. The high pressure can be 5 to 100 times, preferably 10 to 30 times, and most preferably about 17 times the injection pressure.

It is proposed that the injection pressure be 0.01 to 0.5 bar, preferably 0.1 to 0.2 bar, and most preferably about 0.12 bar. In this way, extremely low injection rates can be achieved that may be between $10^{-11}$ to $10^{-13}$ ml of sample fluid per second. Depending on the duration of the injection, one can inject into the individual cells sample amounts in the range between $10^{-11}$ and $10^{-13}$ ml. The size of the cells in question can be less than 100 μm and less than 60 μm.

In the process of the art that was described at the outset, the sample fluid is filled into the microcapillary by immersing the tip into the sample fluid and producing a reduced pressure in the space inside the capillary by withdrawing the syringe piston. The aspiration process takes a relatively long time; also, more sample fluid must be prepared than necessary for the injection. These disadvantages are avoided if, according to the invention, the same fluid is filled in from the other end of the capillary, preferably with a filling capillary that has a lower outside diameter than the inside diameter of the microcapillary by pushing the filling capillary with the output end into the microcapillary all the way into the tip region of the microcapillary. Since the filling of the sample fluid takes place in the region of the capillary tip, there is no danger of entrainment of impurities adhering to the inside wall of the capillary as the sample fluid flows down on it. Such impurities could also lead to the plugging of the tip. Furthermore, in contrast to the known method of the art, there are practically no evaporation losses of sample fluid during filling.

A method for the preparation of the microcapillaries to be used in the injection process is known from the literature reference given at the outset. In this method, both ends of a capillary tube are clamped into the jaws of a drawing apparatus and an area of the tube between the jaws is heated with the aid of a heating coil around the tube and finally the capillary tube is pulled by moving the jaws away from each other. In this way, two microcapillaries with tips are obtained. In this method of the art, the capillary tube is pulled preliminarily by hand in a Bunsen flame so that the abovementioned region of the tube is already constricted to some extent. One of the disadvantages of this is that the micrcapillaries obtained in this way have dimensions which show varying differences, especially they have tips with different inside diameters. Furthermore, this method of production is laborious and relatively time-consuming. On the other hand, microcapillaries with reproducible dimensions can be obtained simply and rapidly if the capillary tubes inserted into the drawing apparatus are uniform over their entire length and have not been prepulled manually.

It is also known from the literature reference given above that the capillary tube should washed before drawing in order to avoid plugging of the tip due to contaminants in the inside space of the capillary. While the washing is carried out with a mixture of $H_2SO_4$ and $HNO_3$ in the process of the art, according to the invention, it is proposed that the capillary tube be washed before pulling for at least 1 hour with ethanol and then preferably dried at about 130° C. for about 30 minutes. Especially good washing results are obtained in this way.

Furthermore, it was found advantageous to render the capillary tube water-repellant before drawing, preferably by treaatment with dimethyldichlorosilane in ethanol or with siliconization solution in ether (1:3).

The invention is also concerned with a device for carrying out the injection process. It is known from the abovementioned literaure reference that the injection pressure can be produced by a manually operated syringe. The disadvantage of this is that, in practice, the injection pressure cannot be adjusted reproducibly to a predetermined constant value. Also, there is no possibility of automatic operation. In order to avoid these disadvantages, the device according to the invention is characterized by at least one pressure source for constant pressure, preferably in the form of a compressed gas cylinder.

In order to be able to inject as many cells as possible per unit time, the operation should be as simple as possible. We achieved this with a single-knob operation when, as proposed by the invention, a manually operated three-way valve is connected between at least one pressure source and the microcapillary in such a way that in the first position of the valve, the holding pressure is applied to the microcapillary, while in the second position of the valve, the injection pressure is applied and, in a third position of the valve, the high pressure is applied. The three-way valve can be operated with one hand and the micromanipulator for the microcapillary can be operated with the other hand. Injection rates of 400 to 800 cells per hour can be reached without special training and without long practice.

A separate holding pressure source can be saved if, according to the invention, a high-pressure source and an injection-pressure source are provided which are connected through the high-pressure line or injection pressure line with a common main line that ends in the microcapillary, whereby a nonreturn valve, possibly opening into the main line, is included in the injection pressure line and the three-way valve is included in the high-pressure line, and, furthermore, the three-way valve is provided with a third connection with a choke which is connected with injection pressure source in the first valve position to reduce the pressure in the main line to the holding pressure.

The nonreturn valve provided in the injection pressure line makes it possible to connect a pressure manometer into the injection pressure line to control the injection pressure and possibly the holding pressure.

In order to prevent sudden expulsion of the sample fluid under the action of the high pressure during injection by inadvertent switching of the three-way valve into the third position, one can use a first two-way valve in the high-pressure valve as well as a second two-way valve in an auxiliary line that has a choke arrangement, instead of the three-way valve, whereby the auxiliary line is either connected with the main line permanently or is connected to the third outlet of the first two-way valve that can be connected to the injection pressure source. The second two-way valve then serves exclusively to switch between the holding pressure and the injection pressure, thus eliminating operating errors. Continous fine adjustment of the holding pressure is possible if the choking position is designed as a regulating valve.

According to the invention, it is recommended that the second two-way valve be foot-operated so that the operator has both hands free during the injection of the cells to operate the manipulator or the microscope.

The separate injection pressure source can be eliminated if the injection pressure source is constructed from a regulated output of the high-pressure source.

In order to facilitate maintenace work, for example, the replacement of microcapillaries, a relief valve may be provided which is connected to the main line.

Furthermore, an auxiliary line provided with a check valve may be connected to the main line to permit connection to an additional pressure source and/or a vaccum source. The vaccum source may be used for aspirating the device for the purposes of cleaning or to check for leaks.

The invention will be explained below with the aid of the drawing using practical examples.

The following are shown:

Figure 1:
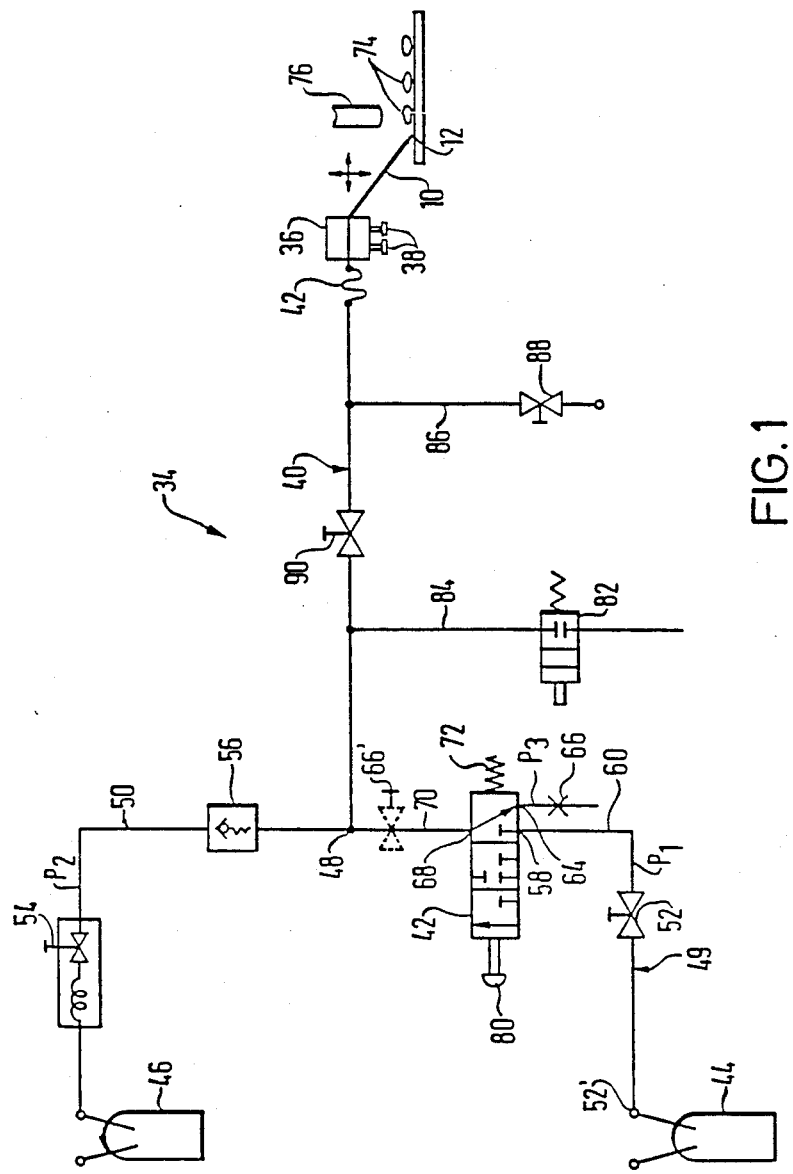
FIG. 1 is a schematic view of the first mode of execution of the injection device according to the invention.

The injection device according to the invention is especially suitable for the injection of sample fluids into living cells and very small sample volumes per cell can be reached, in the region from $10^{-11}$ to $10^{-13}$ ml. The injection must be performed rapidly and simply, so that even after short training an inoculation rate of 400 to 800 cells/h can be reached. The device according to the invention operates extremely reliably since the danger of plugging of the capillary tip is reduced significantly and, moreover, replacement of a microcapillary including preparation and filling of the new microcapillary can be carried out within approximately a few minutes. The injection device for manual operation described below can be set up for automatic operation without any problem.

The microcapillary designated in FIGS. 1 to 4 with 10, having a drawn-out tip 12, is prepared in the following manner. A thin glass tube with a length of about 10 cm, an inside diameter of 0.7–0.8 mm and an outside diamter of 1.0 mm is first washed, namely by treating the tube for about one hour with ethanol then allowing it to drain and finally drying it at 130° C. for about 30 minutes. In addition to that, the capillary tube can be made water-repellant (hydrophobic) by placing it into a 1 to 2% solution of dimethyldichlorosilane in ethanol and allowing this solution to act on it for about 1 hour at 130° C. A siliconization solution (manufactured by, for example, SERVA) in ether (1:3) can also be used.

Then the capillary is placed into a drawing device, not shown, namely by clamping both ends of the tube in the tension jaws of the drawing device. Such a drawing device is represented, for example, in the abovementioned literature reference. The tensional force action on the tension jaws is adjusted to the smallest value and a current is applied to the heating coil that surrounds the middle of the tube, for example, applying a current of 5.7 to 5.8 A when the drawing device of the Company E, Leitz, Wetzlar, is used. As a result of the heating by the heating coil, the glass begins to flow in this region. Under the tensional force of the tension jaws, a constriction is formed so that one obtains finally two halves of the tube, each of which forms a microcapillary with a tip. The outside diamter of the capillary tube is 1 $\mu$m, and the inside diameter is 0.5 $\mu$m. Since the drawing parameters remain constant (tensional force of the drawing jaws; heating current; dimensions of the tube used) microcapillaries with reproducible dimensions are obtained.

Figure 4:
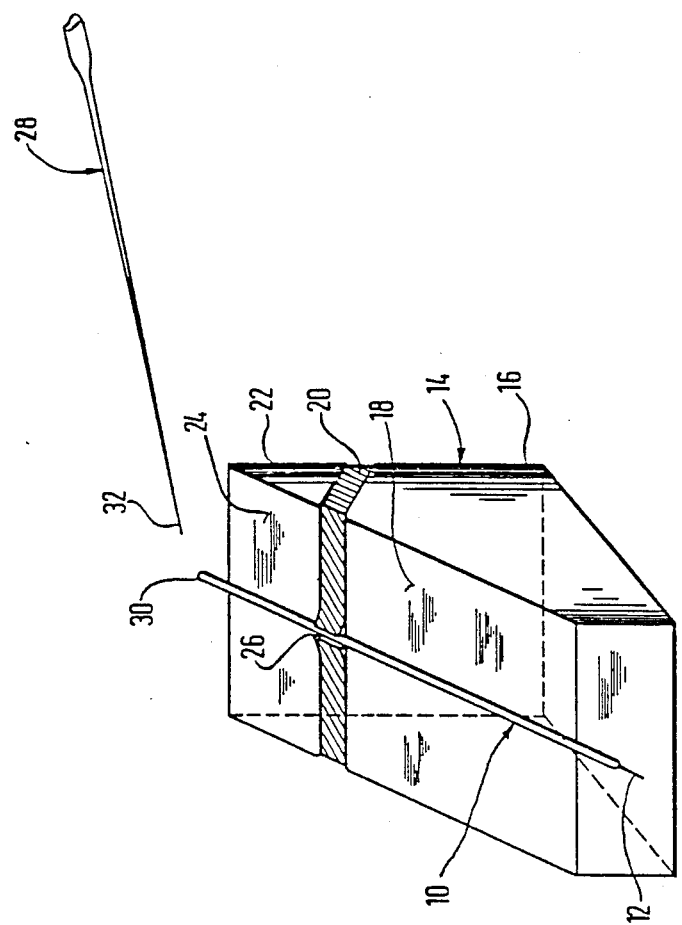
FIG. 4 is a schematic representation of a microcapillary shortly before the beginning of the filling process.

The microcapillary 10 obtained in this way is then introduced into a holder 14 shown in FIG. 4. This consists of a wedge-shaped basic structure 16, one of the wedge surfaces of which lies on the base and the other wedge surface 18 which is inclined to the horizontal serves as support for microcapillary 10. The tip of the wedge is cut off so that when microcapillary 10 is placed onto wedge surface 18 with the tip 12 pointing down, damage to tip 12 is avoided. In the region of the upper end of wedge surface 18, the basic structure 16 is cut off again at an angle; an intermediate rubber layer 20 is glued onto the slanting surface produced in this way;

layer 20 carries a supporting top 22, which is also wedge-shaped and which, together with basic structure 16, completes the wedge-shape of holder 14. Consequently, wedge surface 18 of basic structure 16 continues in wedge surface 24 of supporting top 22. Now, microcapillary 10 is placed onto surfaces 18 and 24 and in this way it lies in a vertical plane which is perpendicular to surfaces 18 and 24. For example, microcapillary 10 is glued onto surfaces 18 and 24. In the example shown, for the sake of simplicity, microcapillary 10 is clamped into groove 26 which is formed by intermediate rubber layer 20 which somewhat protrudes beyond surfaces 18 and 24.

Next, sample fluid is filled into microcapillary 10, for example, 0.1 to 1 μl of a sample fluid. As sample fluid, we can consider, for example, a solution 0.02 to 1 mg of DNA per ml, which has been centrifuged previously for about 10 minutes at 10,000 g or higher. A filling capillary 28 in the form of a thin glass tube with an outside diameter of 0.12 mm and an inside diamter of 0.1 mm serves for filling this sample fluid. Such small glass tubes are available as x-ray glass cylinders. Filling capillary 28 is introduced carefully to capillary end 30 of microcapillary 10 which is at the opposite end from tip 12 and is pushed in until filling capillary tip 32 reaches the region of tip 12 in the inside of microcapillary 10. Then the sample fluid is released.

With another filling capillary with an outside diamter of approximately 0.52 mm and an inside diamter of 0.5 mm, a one or more centimeter high liquid column of a heavy paraffin oil can be layered on top of the sample fluid in the inside space of the capillary. Both filling capillaries are washed before use in the same manner as the microcapillary is.

Now, filled microcapillary 10 can be introduced into the injection device which is generally designated with 34 and is shown in a rough schematic drawing in FIG. 1. For this purpose, microcapillary 10 is clamped into micromanipulator 36, shown symbolically. This micromanipulator permits capillary tip 12 to move in all three coordinates in space. Two knobs 38 are indicated in FIG. 1. The inside space of the capillary is connected to a high-pressure main line 40 through capillary end 30; a flexible intermediate line 42 between manipulator 36 and main line 40, which permits the movement of micromanipulator 36, is shown in FIG. 1. Three different gas pressures can be applied to main line 40 and thus to the inside space of the capillary, as desired; a high pressure $p_1$, an injection pressure $p_2$ and a holding pressure $p_3$. A single valve serves for switching from one pressure to the other, namely three-way valve 42, the switching functions of which are shown in FIG. 1. Two pressure sources are provided in the form of compressed air or nitrogen cylinders, a high-pressure source 44 as well as an injection pressure source 46. High-pressure feed line 49 connects high-pressure source 44 with branching point 48 of main line 40; correspondingly, injection pressure feed line 50 connects injection pressure source 46 with the same branching point 48 of main line 40. A manually adjustable regulating valve (pressure-reducing valve or regulator valve) 52 in high-pressure feed line 49 (or at high-pressure source 44) permits accurate adjustment of the high pressure $p_1$ to a value of, for example, 2 bar. If necessary, pressure $p_1$ can also be regulated electronically. Correspondingly, regulating valve 54 (pressure reducing valve or regulator) 54 is incorporated into line 50 for accurate adjustment of pressure $p_2$ to 0.12 bar. Nonreturn valve 56 is inserted between regulating valve 54 and branching point 48 in line 50. This valve opens in the direction to point 48. The switching function of three-way valve 42 incorporated in line 49 between regulating valve 52 and branching point 48 can be seen from FIG. 1. Three connections of valve 42 are in use, a first connection 58, which is connected to line portion 60 of line 49, this portion leading to regulating valve 52, connection 64 next to it, which is regulated (shown symbolically in FIG. 1 by regulating point 66) as well as a third connection, 68, which is opposite to connection 58 and from which line portion 70 of line 49 begins, this portion leading to braching point 48.

In the first position or rest position of valve 42, shown in FIG. 1, connection 58 is closed but connection 68 is connected with connection 64. Consequently, regulating point 66 is connected to injection pressure source 46. Regulating point 66 is adjusted so that a pressure $p_3$ is established before the regulating point, that is, in line 70 and thus in main line 40. Pressure $p_3$, designated as holding pressure, is 0.03 bar. For accurate adjustment of holding pressure $p_3$, regulating point 66 may be constructed in the form of a corresponding regulating valve. However, another regulating valve (pressure-reducing valve or regulator) 66' can be inserted in line portion 70 between valve 42 and braching point 48, this valve permitting accurate adjustment of holding pressure $p_3$. By fully opening the regulator 66', high pressure $p_1$ can be applied to main line 40.

Now, if valve 42 is switched to a second or middle position, then, correspondingly, the valve body, shown symbolically in FIG. 1, moves to the right into a middle position, against the force of valve spring 72. Now, all connections, 58, 64 and 68 of valve 42 are closed, so that the pressure in line 70 and, therefore, also in main line 40, is adjusted to injection pressure $p_2$.

Finally, when valve 42 is switched into its third position, where the valve body assumes its extreme right position in FIG. 1, connections 58 and 68 are connected to each other but connection 64 is closed. Line portion 70 and thus main line 40 are then connected with high-pressure source 44 and are at pressure $p_1$. Nonreturn valve 56 prevents damage to regulating valve 54 and to injection source 46. Regulating valve 52 can also be omitted in case a pressure-reducing valve 52' indicated in FIG. 1, that is usually provided for pressure sources in the form of pressurized cylinders, is provided, which valve reduces the pressure inside the cylinder from 10 to 150 bar to 0 to 7 bar. In this case, pressure-reducing valve 52' is to be adjusted so that in the third position of valve 42, the pressure in line portion 70 assumes exactly the predetermined value $p_1$.

After the incorporation of microcapillary 10 into micromanipulator 36, first high pressure $p_1$ is applied to the inside space of the capillary (third valve position) in order to fill tip 12 rapidly and to make tip 12 freely passable if necessary. Then holding pressure $p_3$ is applied to the inside space of the capillary. This pressure is chosen so that first of all, substantially no sample fluid flows out from tip 12 and, secondly, nothing can enter into capillary tip 12 from the outside. Now the capillary tip is inserted into one of cells 74, which are shown in an exaggerated size in FIG. 1, by appropriate operation of micromanipulator 36 with observation through a microscope, the microscope objective 76 of which is shown as a broken part in FIG. 1. As soon as tip 12 is inside the cell (in the cytoplasm or in the cell nucleus), injection pressure $p_2$ (second valve position) is applied to the inside space of the capillary which causes a flow of the sample fluid from tip 12. The rate of flow is between $10^{-11}$ and $10^{-13}$ ml per second. Valve 42 is kept in its second position for a time period depending on the desired injection volume and is then released so that the valve will return to the rest position according to FIG. 1 and holding pressure $p_3$ will be applied to the inside space of the capillary. Microcapillary 10 is then moved to the next cell, 74, and this is inoculated in the manner described above.

If it is not certain if tip 12 is completely free, high pressure $p_1$ (third valve position) can be applied to the inside space of the capillary in order to "blow out" tip 12.

Operation of valve 42 can be performed, for example, through a valve operating knob 80 shown in FIG. 1, the knob being displaceable against the force of spring 72.

A decompression valve 82 in the form of a two-way valve is incorporated into auxillary line 84, which opens into main line 40, to permit decompression of device 34. Furthermore, an additional line 86 opening into main line 40 is provided with a check valve 88 to permit connection, as desired, to an additional pressure or vaccum source, for example, an aquarium pump which can also be used as a pressure and/or vacuum source. A check valve or regulating valve 90 is incorporated into main line 40 between the entry points of lines 84 and 86. This vlaue permits the simultanteous adaptation of pressures $p_1$, $p_2$ and $p_3$ to the particular viscosity of the sample fluid.

Figure 2:
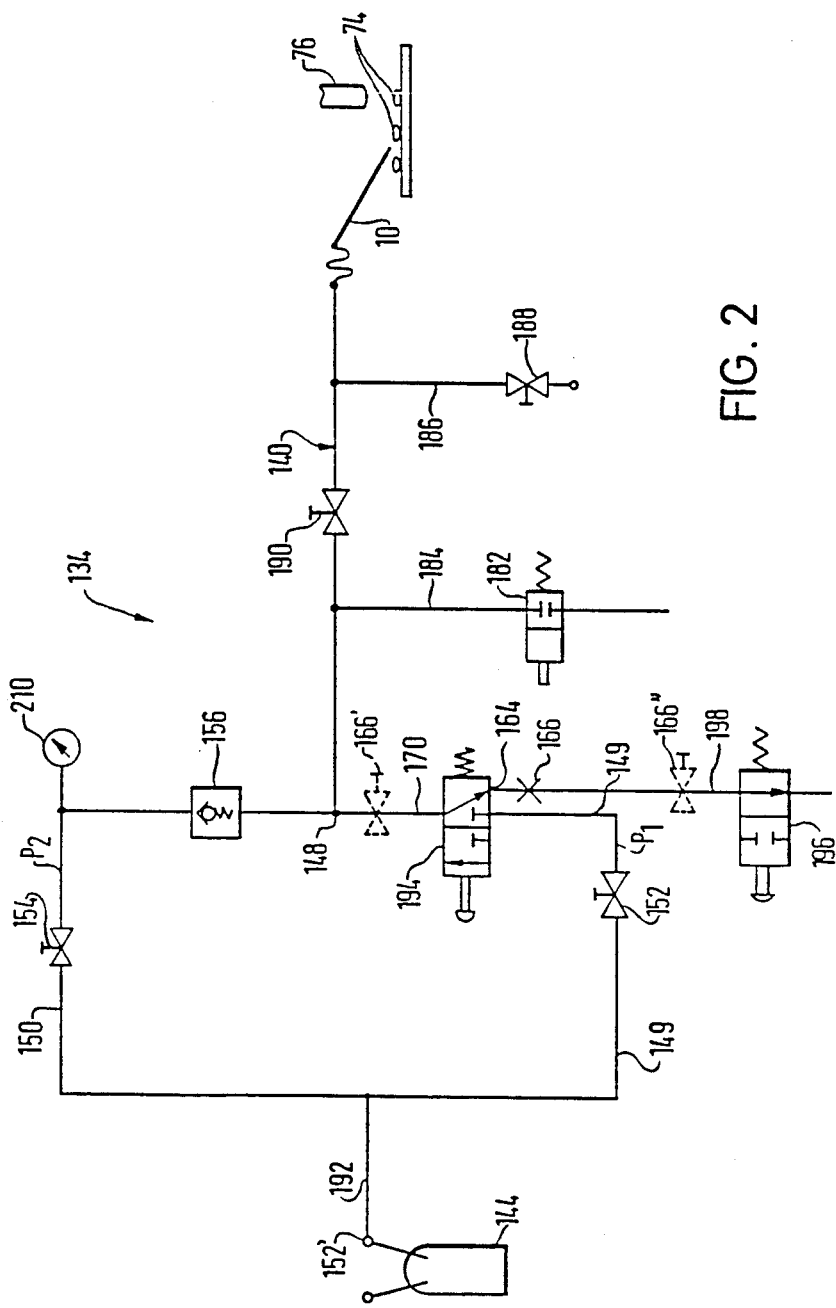
FIG. 2 is a schematic view of a second mode of execution.

FIG. 2 shown another mode of execution of the injection device according to the invention, which is designated with 134. The components in FIG. 2 that correspond to those in FIG. 1 are designated with the same reference numbers with 100 added to them. In the case of injection device 134, only a single pressure source, namely high-pressure source 144 is required. An initial line, 192, starting from high-pressure source 144 continues as two parallel lines 149 and 150, which corresponds to high-pressure line 49 of injection-pressure line 50 according to FIG. 1 and which are finally connected to branching point 148 of main line 140. Again, a regulating valve 152 is included in line 149 and this valve permits exact adjustment of high-pressure $p_1$ in the connected line portion. Correspondingly, regulating valve 154 as well as nonreturn valve 156 are included in line 150 whereby nonreturn valve 156 prevents damage of manometer 210 (for pressure $p_2$) connected between valve 154 and 156 by the higher pressure $p_3$. Regulating valve 154 permits accurate adjustment of pressure $p_2$. Now the three-way valve 42 according to FIG. 1 could be built into branch line 170 between regulating valve 152 and branching point 148. However, in FIG. 2, this is replaced by two two-way valve, a first two-way valve 194 and a second two-way valve 196. The two switching positions of the first two-way valve 194 connected in line 170 can be seen in FIG. 2. In the rest position, the connection between regulating valve 152 and branching point 148 is broken, but regulating valve outlet 164 is at $p_2$. Regulating valve outlet 164, the regulating point 166 of which is shown again symbolically, is connected to two-way valve 196 through connecting line 198. The rest position of valve 196, shown in FIG. 2, the valve is open, so that holding pressure $p_3$ is set up in main line 140. However, when valve 196 is switched to the other position, connecting line 198 is closed so that the injection pressure $p_2$ will be built up in main line 140. Therefore, by operating valve 196, one can switch between the injection pressure $p_2$ and holding pressure $p_3$ without the danger of inadvertent switching to high-pressure $p_1$. In order to switch to high-pressure $p_1$, it is necessary to operate the first two-way valve 194. In order to permit accurate continuous adjustment of holding pressure $p_3$, regulating point 166 can again be constructed using regulating valve 166", which is indicated in FIG. 2 with dashed lines. This latter regulating valve is inserted between the two two-way valves 194 and 196 in line 198. However, corresponding to the arrangement in FIG. 1, one can also include a regulating valve 166' into line 170 between valve 194 and branching point 148. Finally, possibly even regulating valve 152 can be omitted if the pressure-reducing valve 152' is sufficiently accurate for adjusting high-pressure $p_1$.

Also, in the arrangement according to FIG. 2, one can provide a decompression valve 182 to relieve installation 134, incorporated into an auxiliary line 184 that is connected to main line 140. A nonreturn valve or regulating valve 190 is also incorporated in main line 140 and there is finally an auxiliary line 186 with check valve 188.

Figure 3:
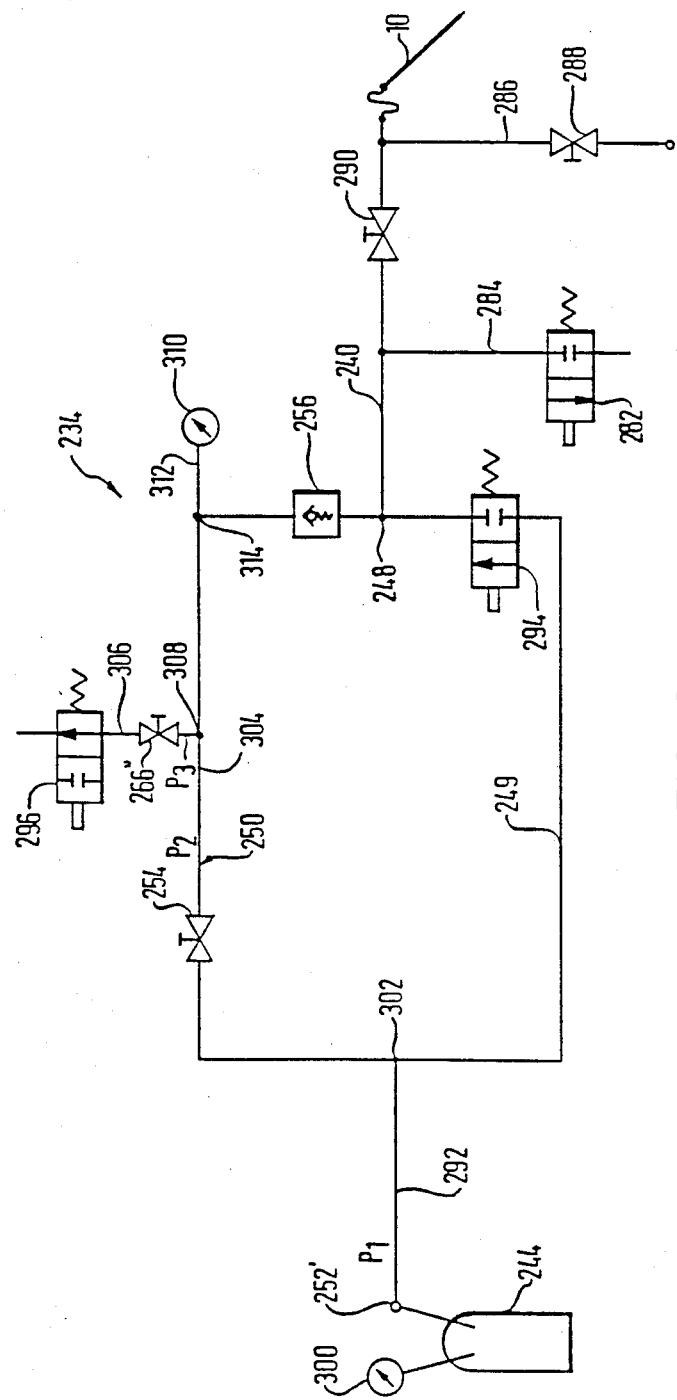
FIG. 3 is a schematic view of a further mode of execution.

Injection device 234 shown in FIG. 3 is constructed similarly to injection devices 34 and 134 according to FIGS. 1 and 2. The structural elements in FIG. 3 that correspond to those in FIG. 1 are given the same reference number, but always increased by 200.

Similarly to the arrangement in FIG. 2, device 234 according to FIG. 3, needs only a single pressure source, namely high-pressure source 244. A pressure-reducing vlave 252' at pressure source 244 permits accurate adjustment of high pressure $p_1$ in the connected initial line 292. The adjusted high pressure $p_1$ can be read on manometer 300 provided on pressure-reducing valve 252'. Finally, initial line 292 branches out at branching point 302 and continues as two parallel lines 249 and 250 which are finally combined again in another branching point 248 and open to main line 240 connected there.

A two-way valve 294 is included in lower line 249 in FIG. 3 and when this valve is in its rest position, shown in FIG. 3, line 249 is closed. When two-way valve 294 is switched, it will permit passage so that high-pressure $p_1$ will be set up at branching point 248 and thus in main line 240.

The upper line 250 contains a regulating valve (precision low-pressure reducing valve, for example, Fairchild Industry, model 10), 254, to adjust the injection pressure $p_2$ in the connected line portion 304 of line 250. In the direction of flow, after regulating valve 254, an auxiliary line 306 enters into line 250 (connecting point 308, see FIG. 3). A two-way valve 296 is connected in auxiliary line 306 and a regulating valve 266" between this valve and point 308. As can be seen from the reference numbers, the functions of these two valves, 266" and 296, correspond to those of valves 166" and 196 in FIG. 2. Therefore, two-way valve 296 allows passage in its rest position shown in FIG. 3 and serves to lower the pressure in line 250 (after regulating valve 254) to holding pressure $p_3$. Exact adjustment of holding pressure $p_3$ is achieved with the aid of regulating valve 266". It should be emphasized that when pressure $p_3$ is adjusted, this does not influence the valves of pressures $p_1$ and $p_2$. The established valves of pressures $p_2$ and $p_3$ can be read on manometer 310 which is connected to line 250 (connection point 314) through auxiliary line 312. Again, there is nonreturn valve 256 incorporated between connection point 314 and branching point 248, corresponding to FIG. 2. This valve prevents establishment of high-pressure $p_1$ in the line portion of line 250 between regulating valve 254 and nonreturn valve 256 when two-way valve 194 is turned on. Otherwise this would lead to damage of the regulating valve 266" that is adjusted to a lower pressure $p_2$ and possibly of manometer 310.

Finally, a relief valve 282 can be provided again in a corresponding auxiliary line 284 of main line 240 as well as a check valve 288 in an auxiliary 286 opeining into main line 240. Furthermore, we should mention a check valve or regulating valve 290 between the junctions of lines 284 and 286 into main line 240. Finally, main line 240 is joined to microcapillary 10.

In the actual injection process, only two-way valve 296 needs to be operated to switch between injection pressure $p_2$ and holding pressure $p_3$. There is no danger of inadvertent switching to high-pressure $p_1$, since this is connected by operating the other two-way valve 294. Foot operation of two-way 296 may be provided to further simplify operation. Then both hands will be free to operate the micromanipulator and possibly the microscope used for observation.

It is obvious that even in injection device 34 according to FIG. 1, one can use the combination of the two-way valves 194 and 196 (or 294 and 296) instead of three-way valve 42. Valve 42 and 194 are of the two-way type while valve 196 is a one-way valve.

With the aid of the injection devices described above, it is possible to inject very small amounts of sample fluid reproducibly into living cells, for example, for the investigation of the distribution of fluorescently labeled structural proteins or for screening of cloned recombinants.

I claim:

1. A device for supplying constant pressures to a microcapillary to carry out a process of controlled injection of small fluid samples through the microcapillary, said device comprising:
   (A) a main line 240 connected to said microcapillary 10;
   (B) a pressure source 244;
   (C) an injection pressure feed line 250 communicating between said pressure source and said main line;
   (D) a high pressure feed line 249 communicating between said pressure source and said main line, said injection pressure and high pressure feed lines being connected in parallel;
   (E) a first valve 294 in said high-pressure feed line;
   (F) a pressure regulating device 254 in said injection pressure feed line;
   G) a pressure regulating line 306;
   (H) a second valve 296 connected to said injection pressure feed line;
   (I) a pressure regulating device 266" inserted in said regulating line between said second valve 296 and said injection pressure feed line;
   (J) a non-return valve 356 inserted in said injection pressure feed line between the point of attachment of said regulating line and said main line;
   said high pressure feed line being blocked from said main line when said first valve 294 is in a first valve position;
   pressure flow through said pressure regulating device in said regulatory line being permitted when said second valve 296 is in a first valve position, thereby establishing a holding pressure in said main line,
   pressurized flow through said pressure regulating line being blocked when said second valve 296 is in a second valve position, thereby establishing in said main line an injection pressure, and,
   pressurized flow being permitted through said first valve when said first valve 294 is in a second valve position, thereby establising in said main line a high pressure.

2. The device of claim 1 wherein an auxiliary line 286 is connected to said main line and provided with a check valve 288 and connected to an additional pressure source.

3. The device of claim 1 wherein a relief valve 282 is connected to said main line.

4. The device of claims 1 wherein a manometer 370 is inserted in said injection pressure feed line between said injection pressure source and said non-return valve.

5. The device of claims 1 wherein means are provided to operate said second valve 296 in said pressure regulating line by foot.

* * * * *